United States Patent
Racherla et al.

[11] Patent Number: 6,117,833
[45] Date of Patent: Sep. 12, 2000

[54] BLEACHING COMPOSITIONS AND METHOD FOR BLEACHING SUBSTRATES DIRECTLY WITH AIR

[75] Inventors: Uday Shanker Racherla, West Caldwell; Robert Charles Vermeer, Nutley, both of N.J.

[73] Assignee: Lever Brothers Company, New York, N.Y.

[21] Appl. No.: 09/212,621

[22] Filed: Dec. 16, 1998

[51] Int. Cl.$^7$ ............................. C11D 3/00; C11D 3/395; D06L 3/02
[52] U.S. Cl. ................. 510/367; 510/302; 8/111
[58] Field of Search ................... 510/367, 302; 8/111

[56] References Cited

U.S. PATENT DOCUMENTS

| | | |
|---|---|---|
| 1,163,438 | 12/1915 | Muller . |
| 3,822,114 | 7/1974 | Montgomery . |
| 4,006,092 | 2/1977 | Jones . |
| 4,255,273 | 3/1981 | Sakkab ................... 252/102 |
| 4,256,597 | 3/1981 | Sakkab ................... 252/99 |
| 4,434,086 | 2/1984 | Hill et al. . |
| 4,476,041 | 10/1984 | Hill et al. . |
| 4,784,790 | 11/1988 | Disch et al. . |
| 5,234,832 | 8/1993 | Disch et al. . |
| 5,478,356 | 12/1995 | Kaaret ................... 8/111 |
| 5,527,769 | 6/1996 | Winter et al. . |
| 5,552,379 | 9/1996 | Winter et al. . |
| 5,863,879 | 1/1999 | Zirnstein et al. ........... 510/360 |
| 5,882,355 | 3/1999 | Koek ................... 8/111 |

FOREIGN PATENT DOCUMENTS

| | | |
|---|---|---|
| 993 755 | 7/1976 | Canada . |
| 0 050 015 | 4/1982 | European Pat. Off. . |
| 0 125 103 | 11/1984 | European Pat. Off. . |
| 2148302 | 3/1973 | France . |
| 63-92698 | of 1988 | Japan . |
| 97/34986 | 9/1997 | WIPO . |
| 97/38074 | 10/1997 | WIPO . |

*Primary Examiner*—Yogendra Gupta
*Assistant Examiner*—John M Petruncio
*Attorney, Agent, or Firm*—Milton L. Honig

[57] ABSTRACT

A bleach composition and a method for bleaching stains is provided, the composition including a $C_7$–$C_{20}$ aromatic aldehyde and an imide, the latter being particularly N-hydroxyphthalimide. Air is employed as a source of oxygen which combines with the aldehyde to form the bleach active species. Peroxides, inorganic persalts and bleach precursors are unnecessary elements for the bleach systems of this invention.

14 Claims, No Drawings

BLEACHING COMPOSITIONS AND METHOD FOR BLEACHING SUBSTRATES DIRECTLY WITH AIR

BACKGROUND OF THE INVENTION

1. Field of the Invention

The invention concerns compositions and processes for bleaching substrates directly with air.

2. The Related Art

Oxygen bleaches are well known for their ability to remove stains from substrates. Traditionally the substrate is subjected to hydrogen peroxide or substances which can generate hydroperoxyl radicals. The latter may be inorganic or organic peroxides. Generally these systems must be activated. A method of activation is to employ wash temperatures of 60° C. or higher. Unfortunately, these high temperatures often lead to inefficient cleaning. They can also cause premature damage to the substrate.

A preferred approach to generating hydroperoxyl bleach radicals is the use of inorganic peroxides coupled with organic precursor compounds. These systems are employed for many commercial laundry powders. European systems are based on tetraacetyl ethylenediamine (TAED) as the organic precursor coupled with sodium perborate or sodium percarbonate. Well known in the United States are laundry bleach products based on sodium nanonyloxybenzenesulphonate (SNOBS) as the organic precursor coupled with sodium perborate. Precursor systems are generally effective yet they still exhibit several disadvantages. For example, organic precursors are moderately sophisticated molecules requiring multi-step manufacturing processes resulting in high capital costs. Secondly, precursor systems have large formulation space requirements; a significant percent of a laundry powder must be devoted to the bleach components leaving less room for other active ingredients and complicating development of concentrated powders. Moreover, precursor systems do not bleach very efficiently in countries where consumers have wash habits entailing low dosage, short wash times, cold temperatures and low wash liquor to cloth ratios.

A long cherished dream has been to use air directly as the oxygen source. Air would avoid costly synthesized organic precursors. Unfortunately, air is kinetically inert towards bleaching substrates due to the spin barrier restriction and exhibits no bleaching ability. Recently some progress has been made in this area.

WO 97/38074 reports use of molecular oxygen (air) for oxidizing stain from fabrics. It was discovered that fabrics can be bleached by bubbling air through an aqueous solution containing an aldehyde. A broad range of aliphatic, aromatic and heterocyclic aldehydes were reported to be useful, particularly para-substituted aldehydes such as 4-methyl-, 4-ethyl- and 4-isopropyl benzaldehyde. It was also necessary in these systems to employ a radical initiator. A broad range of initiators were disclosed including N-hydroxysuccinimide, various peroxides and transition metal coordination complexes. While this disclosure appears to be a step-change in bleach chemistry, it is clear that more work is required to reveal the optimum system.

Accordingly, it is an object of the present invention to provide an optimum bleaching system with improved stain removal efficacy based on air or molecular oxygen.

Another object of the present invention is to provide a bleaching system which is cost-effective and environmentally friendly.

Still another object of the present invention is to provide a bleaching system based on air that is operable under harsh wash conditions which includes low temperatures, short contact times and low dosage requirements.

Yet another object of the present invention is to provide an improved hygiene or antimicrobial benefit coupled with a reduction in dye transfer damage.

These and other objects of the present invention will become more readily apparent from the following summary and detailed description.

SUMMARY OF THE INVENTION

A bleaching composition is provided which includes:

(i) an effective amount for stain removal of a $C_7$–$C_{20}$ aromatic aldehyde;

(ii) air as a primary source of oxygen atoms to combine with the aldehyde; and (iii) an effective amount to activate the aldehyde of an imide having the formula:

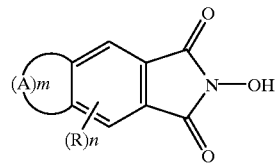

wherein

A is $CX_q$ and X is selected from the group consisting of hydrogen, $C_1$–$C_5$ alkyl, a heteroatom substituent and mixtures thereof, where q is independently 1 or 2;

R is a moiety selected from the group consisting of hydrogen, alkyl, cycloalkyl, aryl, alkoxy, hydroxy, acyloxy, halo, carboxy, amino, quaternary amino, sulpho, phospho, cyano radicals and mixtures thereof;

m and n independently range from 0 to 4.

Furthermore, a method for bleaching stains from substrates is provided by treating the substrates with air, an aromatic aldehyde and an imide in an aqueous system.

DETAILED DESCRIPTION OF THE INVENTION

Now it has been discovered that stains can be removed simply by air oxidation through the intermediacy of a $C_7$–$C_{20}$ aromatic aldehyde in conjunction with certain aromatic imides. Each of these elements will be described in more detail below.

An essential feature of the present invention is a $C_7$–$C_{20}$ aromatic aldehyde. Particularly advantageous are aromatic aldehydes selected from those having a calculated logP ranging from about 2 to about 3. The term logP is the mathematical log value of the partition coefficient for solubility of the aldehyde between water and 1-octanol. It is a property of a two-phase system in which 1-octanol and water are in equilibrium, at a fixed temperature, and an organic substance is distributed between these phases. LogP is best defined as the equilibrium distribution or the ratio of an organic substance in the 1-octanol phase to that in the water phase. In general, logP tends to be small for polar hydrophilic substances and large for nonpolar hydrophobic substances. Thus logP provides a measure of the hydrophilic vs. hydrophobic nature (HLB balance) of a compound, which is an important consideration in assessing solubility. We have found that aldehydes outside the calculated logP range of about 2 to 3 do not bleach and are ineffective. Even more advantageous are aromatic aldehydes that are liquids and have a total carbon content from 7 to 15, preferably from 7 to 10, and optimally from 8 to 9 carbon atoms. Examples, of specific aromatic aldehydes which are particularly effective include: 2-methylbenzaldehyde, 3-methylbenzaldehyde, 4-methylbenzaldehyde, 2-chlorobenzaldehyde, 2,3-dimethylbenzaldehyde, 2,4-dimethylbenzaldehyde, 2,5-dimethylbenzaldehyde, 3,6-dimethylbenzaldehyde, 3,4-dimethylbenzaldehyde, 3,5-dimethylbenzaldehyde, 4,5-dimethylbenzaldehyde, 4,6-dimethylbenzaldehyde, 5,6-dimethylbenzaldehyde, 2-ethylbenzaldehyde, 2-trifluoromethylbenzaldehyde, 4-ethylbenzaldehyde, 3-ethylbenzaldehyde, 2,3,4-trimethylbenzaldehyde, 2,3,5-trimethylbenzaldehyde, 2,3,6-trimethylbenzaldehyde, 2,4,5-trimethylbenzaldehyde, 2,4,6-trimethylbenzaldehyde, 2,5,6-trimethylbenzaldehyde, 3,4,5-trimethylbenzaldehyde, 3,4,6-trimethylbenzaldehyde, 3,5,6-trimethylbenzaldehyde, 4,5,6-trimethylbenzaldehyde and the like.

For purposes of this invention it is to be understood that the term aromatic aldehyde encompasses substituted aromatic rings. Illustrative but not limiting examples of substituted groups are alkyl (particularly methyl and ethyl), trifluoromethyl, carboxy, phospho, sulpho, chloro, bromo, fluoro, cyano, alkoxy, nitro, amino, quaternary ammonium, hydroxyalkyl and combinations thereof. Of course, the choice of substituent must allow the aldehyde to fall within the acceptable calculated logP value of about 2 to about 3 and other criteria previously specified for optimum bleaching performance.

Amounts of the aromatic aldehyde may range from about 0.01 to about 80%, preferably from about 0.1 to about 50%, more preferably from about 0.5 to about 20%, optimally from about 1 to about 5% by weight of the bleaching composition.

A second essential feature of the present invention is the presence of an aromatic imide of the general structure:

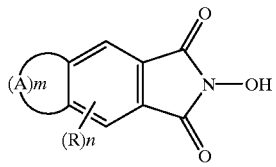

wherein
A is $CX_q$ and X is selected from the group consisting of hydrogen, $C_1$–$C_5$ alkyl, a heteroatom substituent and mixtures thereof, where q is independently 1 or 2;
R is a moiety, which if hydrocarbyl may have from 1 to 7 carbon atoms, and is selected from the group consisting of hydrogen, alkyl, cycloalkyl, aryl, alkoxy, hydroxy, acyloxy, halo, carboxy, amino, quaternary amino, sulpho, phospho, cyano radicals and mixtures thereof;
m and n may independently range from 0 to 4.

Particularly preferred substituents are methyl, ethyl, isopropyl, chloro, trifluoromethyl, methoxy, acetyl and cyclic groups such as pyridyl, naphthyl, phenyl, furanyl and indolyl radicals. Most preferred is the unsubstituted generic structure where m and n are both 0; this material is known as N-hydroxyphthalimide (NHPI). Examples of other potentially useful imides have structures as outlined below.

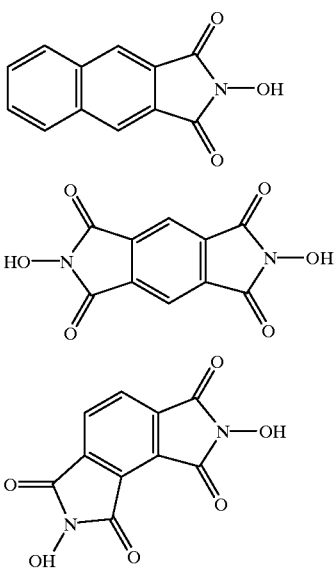

Amounts of the imide may range from about 0.001 to about 65%, preferably from about 0.01 to about 7%, more preferably from about 0.01 to about 1% by weight of the bleaching composition. The weight ratio of aldehyde to imide may range from about $1\times10^8:1$ to about $1\times10^6:1$, preferably from about $1\times10^4:1$ to about 1:1, more preferably from about 1000:1 to about 10:1.

Bleach systems of the present invention may be employed for a wide variety of purposes. These include cleaning hard surfaces, food utensils, kitchenware, floors, bathtubs, hair, carpets, dentures and fabrics. Most especially the systems are useful in the cleaning of laundry and kitchenware. When intended for such purpose, the aldehyde and imide of the present invention may usually be combined with surface-active materials, detergency builders and other known ingredients of detergent formulations.

The surface-active material (i.e. surfactants or cleansing agents) may be naturally derived, or synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from 0.5 to 40% by weight of the composition, most preferably 4 to 25%.

Synthetic anionic surface-actives are usually water-soluble alkali metal salts of organic sulphates and sulphonates having alkyl radicals containing from about 8 to about 22 carbon atoms.

Examples of suitable synthetic anionic detergent compounds are sodium and ammonium alkyl sulphates, especially those obtained by sulphating higher ($C_8$–$C_{18}$) alcohols produced for example from tallow or coconut oil; sodium and ammonium alkyl ($C_8$–$C_{20}$) benzene sulphonates, sodium alkyl glyceryl ether sulphates, especially those ethers of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; sarcosinate salts; alkane monosulphonates such as those derived by reacting alpha-olefins ($C_8$–$C_{20}$) with sodium bisulphite and those derived by reacting paraffins with $SO_2$ and $Cl_2$ and then hydrolyzing with a base to produce a random sulphonate; sodium and ammonium $C_7$–$C_{12}$ dialkyl sulfosuccinates; and olefin sulphonates, which term is used to describe the material made by reacting olefins, particularly $C_{10}$–$C_{20}$ alpha-olefins, with $SO_3$ and then neutralizing and hydrolyzing the reaction product, sulphated or sulphonated alkyl polyglucosides, sulphated alkyl methyl glucamides, sulphated lactobionamides and combinations thereof. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6$–$C_{22}$) phenols, generally 5–25 EO, i.e. 5–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglucosides, long chain tertiary amine oxides, and fatty amido polyols such as alkyl methyl glucamides and alkyl lactobionamides.

Amphoteric or zwitterionic surface-active compounds such as alkylamidopropyl betaines can also be used in the compositions of the invention. If any amphoteric or zwitterionic detergent compounds are used, it is generally in small amounts in compositions based on the much more commonly used synthetic anionic and nonionic actives.

Soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between 0.5 and 25% by weight, with lower amounts of 0.5 to 5% being generally sufficient for lather control. Amounts of soap between 2 and 20%, especially between 5 and 15, are used to give a beneficial effect on detergency. This is particularly valuable in compositions used in hard water where the soap acts as a supplementary builder.

In systems where anionic surfactants such as linear alkylbenzene sulphonate are employed, it may be desirable to include a hydrotrope or phase regulant such as alkali metal benzene sulphonate, toluene sulphonate and ethyl benzene sulphonate thereby improving the bleaching effect.

The detergent compositions of the invention will normally also contain a detergency builder. Builder materials may be selected from (1) calcium sequestrant materials, (2) precipitating materials, (3) calcium ion-exchange materials and (4) mixtures thereof.

In particular, the compositions of the invention may contain any one of the organic or inorganic builder materials, such as sodium, potassium, lithium or magnesium salts of tripolyphosphate, pyrophosphate, orthophosphate, carbonate, nitrilotriacetic acid, citrate, carboxymethylmalonate, carboxymethyloxysuccinate, tartrate mono- and di- succinate, oxydisuccinate, bicarbonate, tetraborate, tetraboratedecahydrate, crystalline or amorphous aluminosilicates and mixtures thereof. Most preferred among the builders are the salts of carbonate, sesquicarbonate, bicarbonate and borate as well as zeolite and mixtures thereof.

Polycarboxylic homo- and co-polymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of from about 1 to 80% by weight, preferably from about 10 to 60% by weight.

Upon dispersal in a wash water, the initial amount of aldehyde should range anywhere from about 0.1 to about 30 mmol/liter, preferably from about 1 to about 15 mmol/liter of the aqueous wash liquor. The N-hydroxy imide can range anywhere from about 0.001 to about 10 mmol/liter, preferably from about 0.01 to about 2 mmol/liter. Surfactant when present in the wash water may range from about 0.05 to about 1.0 grams/liter, preferably from about 0.15 to about 0.25 grams/liter. When present, the builder amount may range from about 0.1 to about 3.0 grams/liter.

Often the aldehydes of the present invention are sensitive to certain detergent ingredients as well as to air; they can be protected by encapsulation or some other suitable protective barrier. Methods of encapsulation are described in U.S. Pat. No. 5,385, 959, U.S. Pat. No. 5,441,660 and U.S. Pat. No. 5,434,069. Examples of preferred encapsulation polymers include, but are not limited to, polyvinyl alcohol, polyacrylamide, polyvinyl pyrrolidone, carrageenan, guar gum, xanthan gum and celluloses.

Apart from the components already mentioned, the bleaching compositions of the invention may contain any of the conventional additives in the amounts in which such materials are normally employed in cleaning compositions. Examples of these additives include dye transfer inhibition agents such as polyamine N-oxide polymers, metallo phthalocyanines, and polymers based on N-vinylpyrrolidone and N-vinylimidazole, lather boosters such as alkanolamides, particularly the monoethanolamides derived from palmkernel fatty acids and coconut fatty acids, lather-depressants such as alkyl phosphates and silicones, anti-redeposition agents such as sodium carboxymethylcellulose and alkyl or substituted alkylcellulose ethers, stabilizers such as ethylene diamine tetraacetic acid and phosphonic acid derivatives (Dequest®), fabric softening agents, inorganic salts such as sodium sulphate, and, usually present in very small amounts, fluorescent agents, perfumes, enzymes such as proteases, cellulases, lipases and amylases, germicides and colorants.

The aldehydes in combination with the imide may be useful for removing stains both in consumer type products and for industrial applications. Among consumer products incorporating this invention are laundry detergents, laundry bleaches, hard surface cleaners, toilet bowl cleaners, automatic dishwashing compositions and even denture cleansers. Stained consumer products benefiting from treatment with compositions of this invention may include clothes and other fabrics; household fixtures and appliances such as sinks, toilet bowls and oven ranges; tableware such as drinking glasses, dishes, cookware and utensils; and dentures. Hair colorants may also be formulated with the bleach composition of this invention. The bleaching system of this invention may also be applied to industrial uses such as for the bleaching of wood pulp.

The system of the present invention may be delivered in a variety of product forms including powders, on sheets or other substrates, in pouches, in tablets, in aqueous liquids, or in nonaqueous liquids such as liquid nonionic detergents, aerosol, gel, cream or granular form.

The following examples will more fully illustrate the embodiments of this invention. All parts, percentages and proportions referred to herein and in the appended claims are by weight unless otherwise specified.

EXAMPLE 1

A general outline of the essential steps in our experimental protocol are shown below.

An Outline of the Essential Protocol Steps a) Measure the initial reflectance of the swatches ($R_i$).
b) Saturate the wash solution with air.
c) Wash, rinse and dry the swatches.
d) Measure the final reflectance of the swatches ($R_f$).

All work was conducted in a Tergotometer with 2L stainless steel pots. The swatches were dried flat on a rack in a Kenmore dryer. Each experiment was performed once with 2 replicate pots containing the same aldehyde (average of 2 values), except for the exceptional bleaching aldehydes, which were repeated 3 times with 2 replicate pots containing the same aldehyde (average of 6 values). The conditions utilized were as follows:

Conditions for Saturating the Wash Solution With Air

| | |
|---|---|
| Saturation Time | 15 mins |
| Agitation | 100 rpm |
| Water Volume | 1 L |
| Hardness | None |
| Air Rate | 532 ml/min. |
| Temperature | 25° C. |

Wash Conditions

| | |
|---|---|
| Wash Time | 30 mins |
| Agitation | 100 rpm |
| Water Volume | 1 L |
| Hardness | None |
| Buffer | Carbonate |
| Initiator | N-Hydroxyphthalimide (NHPI, 1 mM) |
| Aldehyde | Aldehyde (15 mM) |
| pH | 8 or 10 |
| Air Rate | 532 ml/min |
| Temperature | 25° C. |
| Test cloths | Tea (BC-1) |
| Ballast | None |
| L/C Ratio | 208:1 |

Rinse Conditions

| | |
|---|---|
| Rinse Time | 3 mins |
| Agitation | 100 rpm |
| Water Volume | 1 L |
| Hardness | None |
| Temperature | 25° C. |
| Replicate Rinses | 2 |

Each Tergotometer Pot was filled with 1 liter of milli-Q-water containing carbonate buffer solution which was saturated for 15 minutes with air under agitation at 25° C. Tea stained (BC-1) swatches were washed for 30 minutes in the presence of aldehyde, air and NHPI at pH=8 (25° C.). The corresponding controls (buffer alone, NHPI alone and aldehyde alone) were performed simultaneously. All swatches were rinsed twice for 3 minutes with agitation at 25° C. and dried flat on a rack in a Kenmore with soft heat for 30 minutes.

Bleaching Evaluation

To quantify the degree of stain removal, the reflectance of 4 stained swatches (4 per pot) were measured before and after washing using a Gardner reflectometer (Model #2000) set at 460*nm (*UV filter). The change in reflectance ($\Delta R$) was determined by taking the difference of the swatch before and after each washing. The standard deviation ($\sigma$) and $\Delta\Delta R_{ave}$ was assigned to each experimental group.

$$\Delta R = R_f - R_i$$

$R_i$=Initial reflectance of stained swatch before washing.
$R_f$=Final reflectance of stained swatch after washing.

$$\Delta R_{aldehyde\ system+control} - \Delta R_{control} = \Delta\Delta R ---2-3x--- \Delta\Delta R_{ave}$$

$\Delta\Delta R_{ave}$=Represents the average bleaching by the aldehyde system.

In general, the larger the $\Delta\Delta R_{ave}$ value, the greater the bleaching and cleaning.

Statistics

Standard Deviation
$(\sigma)=[\Sigma^n(a_j-a_a)^2/N-I]^{0.5}$
$a_j$=actual $\Delta R$
$a_a$=mean $\Delta R$
$\Sigma^n$=sum $(a_j-a_a)^2$ per measurement
N=number of measurements=8

The following table lists aldehydes for which the logP was calculated and (for most) the bleach activity on a tea stain was reported.

TABLE I

The Calculated LogP (−3.40–2.02) and $\Delta\Delta R$ for Group I Aldehydes

| Group I Aldehyde | Calculated LogP | $\Delta\Delta R_{ave}$ on BC-1 at pH = 8 |
|---|---|---|
| D-Glucose | −3.40 ± 0.45 | 0.6 |
| DL-Glyceraldehyde | −1.59 ± 0.39 | −0.8 |
| 4-Formylmorpholine | −1.55 ± 0.34 | 0.1 |
| Glyoxal | −0.67 ± 0.54 | 0.6 |
| 5-Formylfuran-2 sulfonic Acid | −0.61 ± 0.64 | −3.3 |
| Glutaric Dianhydride | −0.33 ± 0.25 | 0.7 |
| 2-Imidazolecarboxy Aldehyde | 0.15 ± 0.57 | −0.5 |
| 1-Formylbenzene-2-sulfonic acid | 0.27 ± 0.87 | 0.5 |
| Phenyl-1,2-dicarboxyaldehyde | 0.51 ± 0.30 | 1.1 |
| Crotonaldehyde | 0.51 ± 0.28 | 0.7 |
| 3-Aminobenzaldehyde | 0.67 ± 0.26 | — |

TABLE I-continued

The Calculated LogP (−3.40–2.02) and ΔΔR for Group I Aldehydes

| Group I Aldehyde | Calculated LogP | ΔΔR$_{ave}$ on BC-1 at pH = 8 |
|---|---|---|
| 1 Formylbenzene-3-sulfonic acid | 0.67 ± 0.62 | — |
| 1-Formylbenzene-4-sulfonic acid | 0.72 ± 0.62 | — |
| Isobutyraldehyde | 0.72 ± 0.23 | 0.4 |
| 2-Furfural | 0.73 ± 0.26 | 0.2 |
| 2-Carboxybenzaldehyde | 0.77 ± 0.27 | — |
| 4-Aminobenzaldehyde | 0.91 ± 0.26 | — |
| n-Butyraldehyde | 0.91 ± 0.22 | 0.6 |
| 3-Hydroxybenzaldehyde | 1.25 ± 0.25 | 0.8 |
| 2-Aminobenzaldehyde | 1.31 ± 0.28 | — |
| Phenyl-1,3-dicarboxyaldehyde | 1.34 ± 0.29 | 0.2 |
| 2-Methoxybenzaldehyde | 1.37 ± 0.26 | 0.8 |
| 4-Hydroxybenzaldehyde | 1.39 ± 0.26 | 0.7 |
| n-Pentylaldehyde | 1.44 ± 0.22 | — |
| Phenyl-1,1-dicarboxyaldehyde | 1.49 ± 0.29 | −1.1 |
| 3,5-Dimethoxybenzaldehyde | 1.53 ± 0.35 | 1.4 |
| 4-Nitrobenzaldehyde | 1.56 ± 0.26 | 0.3 |
| 2,6-Dinitrobenzaldehyde | 1.60 ± 0.35 | — |
| 3-Carboxybenzaldehyde | 1.60 ± 0.26 | — |
| 2-Hydroxybenzaldehyde | 1.61 ± 0.26 | 0.4 |
| Benzaldehyde | 1.64 ± 0.24 | 1.5 |
| 3-Methoxybenzaldehyde | 1.65 ± 0.26 | 0.6 |
| 4-Methoxybenzaldehyde | 1.70 ± 0.36 | 1.2 |
| 2-Nitrobenzaldehyde | 1.74 ± 0.26 | 0.1 |
| 4-Carboxybenzaldehyde | 1.75 ± 0.26 | −0.1 |
| 3-Nitrobenzaldehyde | 1.75 ± 0.26 | 1.2 |
| 2-Phenylpropionaldehyde | 1.79 ± 0.21 | 0.1 |
| 2-Fluorobenzaldehyde | 1.79 ± 0.34 | 1.0 |
| 3,5-Dinitrobenzaldehyde | 1.80 ± 0.35 | 0.1 |
| 4-Dimethylaminobenzaldehyde | 1.81 ± 0.26 | 1.0 |
| 4-Fluorobenzaldehyde | 1.85 ± 0.34 | 1.6 |
| 3-Fluorobenzaldehyde | 1.89 ± 0.34 | 0.6 |
| 2-Ethoxybenzaldehyde | 1.90 ± 0.26 | — |
| n-Hexylaldehyde | 1.97 ± 0.22 | 1.6 |
| 3,5-Difluorobenzaldehyde | 2.02 ± 0.44 | 0.9 |

TABLE II

The Calculated LogP (2.10–3.03) and ΔΔR for Group II Aldehydes

| Group II Aldehyde | Calculated LogP | ΔΔR$_{ave}$ on BC-1 at pH = 8 |
|---|---|---|
| 2-Methylbenzaldehyde | 2.10 ± 0.24 | 5.8* |
| 3-Methylbenzaldehyde | 2.10 ± 0.24 | 10.0* |
| 4-Methylbenzaldehyde | 2.10 ± −.24 | 8.3* |
| trans-Cinnamaldehyde | 2.12 ± 0.36 | 1.2 |
| 2,3,5,6-Tetrafluorobenzaldehyde | 2.13 ± 0.60 | 0.3 |
| 4-Methoxy-3-Methylbenzaldehyde | 2.16 ± 0.26 | 0.4 |
| 3-Ethoxybenzaldehyde | 2.18 ± 0.26 | — |
| 4-Ethoxybenzaldehyde | 2.23 ± 0.26 | 0.4 |
| 2-Chlorobenzaldehyde | 2.33 ± 0.26 | 8.7* |
| 4-Chlorobenzaldehyde | 2.40 ± 0.26 | −0.1 |
| 2-Propoxybenzaldehyde | 2.43 ± 0.26 | — |
| 3-Chlorobenzaldehyde | 2.44 ± 0.26 | 1.9 |
| 3-Trifluoromethylbenzaldehyde | 2.57 ± 0.30 | 3.1 |
| n-Heptyladehyde | 2.50 ± 0.22 | 0.8 |
| 2-Bromobenzaldehyde | 2.51 ± 0.34 | 2.1 |
| 3,4-Dimethylbenzaldehyde | 2.56 ± 0.25 | 10.3* |
| 3,5-Dimethylbenzaldehyde | 2.56 ± 0.25 | 9.3* |
| 2,4-Dimethylbenzaldehyde | 2.56 ± 0.25 | 8.9* |
| 2,5-Dimethylbenzaldehyde | 2.56 ± 0.25 | 8.8* |
| 4-Bromobenzaldehyde | 2.57 ± 0.34 | 0.1 |
| 3-Bromobenzaldehyde | 2.61 ± 0.34 | 3.2 |
| 2-Trifluoromethylbenzaldehyde | 2.61 ± 0.31 | 10.2* |
| 4-Trifluoromethylbenzaldehyde | 2.61 ± 0.30 | 0.3 |
| 2-Ethylbenzaldehyde | 2.63 ± 0.24 | — |
| 3-Ethylbenzaldehyde | 2.63 ± 0.24 | — |
| 4-Ethylbenzaldehyde | 2.63 ± 0.24 | 11.5* |
| 3-Propoxybenzaldehyde | 2.71 ± 0.26 | — |
| 4-Propoxybenzaldehyde | 2.76 ± 0.26 | 0.2 |
| 2-Butoxybenzaldehyde | 2.96 ± 0.26 | — |

TABLE II-continued

The Calculated LogP (2.10–3.03) and ΔΔR for Group II Aldehydes

| Group II Aldehyde | Calculated LogP | ΔΔR$_{ave}$ on BC-1 at pH = 8 |
|---|---|---|
| 4-Isopropylbenzaldehyde | 2.98 ± 0.25 | 1.5 |
| 2,4,6-Trimethylbenzaldehyde | 3.02 ± 0.25 | 6.3* |
| n-Octylaldehyde | 3.03 ± 0.22 | — |

TABLE III

The Calculated LogP (3.10–5.69) and ΔΔR for Group III Aldehydes

| Group III Aldehyde | Calculated LogP | ΔΔR$_{ave}$ on BC-1 at pH = 8 |
|---|---|---|
| 2,6-Dichlorobenzaldehyde | 3.10 ± 0.35 | 0.0 |
| 4-Propylbenzaldehyde | 3.16 ± 0.24 | — |
| 3,5-Dichlorobenzaldehyde | 3.24 ± 0.27 | −0.2 |
| 3-Butoxybenzaldehyde | 3.24 ± 0.26 | — |
| 4-Butoxybenzaldehyde | 3.29 ± 0.26 | — |
| 4-t-Butylbenzaldehyde | 3.33 ± 0.26 | 1.3 |
| 4-Pentyloxybenzaldehyde | 3.49 ± 0.26 | — |
| 4-sec-Butylbenzaldehyde | 3.51 ± 0.25 | — |
| 4-Isobutylbenzaldehyde | 3.51 ± 0.25 | — |
| n-Nonylaldehyde | 3.56 ± 0.22 | 0.1 |
| 4-Butylbenzaldehyde | 3.69 ± 0.24 | 1.3 |
| 3-Phenoxybenzaldehyde | 3.80 ± 0.35 | 1.1 |
| 3-Pentyloxybenzaldehyde | 3.83 ± 0.26 | — |
| n-Decylaldehyde | 4.09 ± 0.22 | 0.6 |
| 3-(4-Methylphenoxy)benzaldehyde | 4.26 ± 0.36 | 0.0 |
| 4-Hexyloxybenzaldehyde | 4.36 ± 0.26 | 0.5 |
| n-Undecylaldehyde | 4.63 ± 0.22 | 0.0 |
| 3-(4-Chlorophenoxy)benzaldehyde | 4.63 ± 0.37 | — |
| 4-Hydroxy-3,5-t-Butylbenzaldehyde | 4.77 ± 0.28 | 0.0 |
| α-Amylcinnamaldehyde | 4.80 ± 0.37 | 1.0 |
| n-Dodecylaldehyde | 5.16 ± 0.22 | 0.2 |
| n-Tridecylaldehyde | 5.69 ± 0.22 | — |

* = Exceptional Bleaching Aldehyde

It is evident from the Tables I–III that only certain aldehydes, and most especially only those aromatic aldehydes in Table II having a logP between about 2 to about 3 provide an exceptional bleaching benefit. The aldehydes of Table II are all liquids and have a total carbon content from about 7 to 10 carbon atoms.

EXAMPLE 2

A series of experiments were conducted to evaluate the bleaching effectiveness of NHPI and related imides. Table IV reports the effectiveness on tea stained cloth swatches by various imide initiators in combination with 4-ethylbenzaldehyde.

TABLE IV

Bleaching on BC-1 by 4-Ethylbenzaldehyde with Various Initiators

| | #1 | #2 | #3 | Average |
|---|---|---|---|---|
| Carbonate Buffer | | | | |
| TEMPO (1 mM) | 1.8 | 1.8 | 1.9 | 1.8 |
| 4-EBA (15 mM) | −0.3 | −0.4 | −0.2 | −0.3 |
| 4-EBA (15 mM) | 0.6 | 0.2 | 0.7 | 0.5 |
| 4-EBA (15 mM) + TEMPO (1 mM) | −0.6 | 0.2 | −0.1 | −0.2 |
| Carbonate Buffer | 2.1 | 1.8 | 2.0 | 2.0 |
| NHSISA (1 mM) | 0.2 | 0.5 | 0.0 | 0.2 |
| 4-EBA (15 mM) | 0.9 | 0.9 | 0.8 | 0.9 |
| 4-EBA (15 mM) + NHSISA (1 mM) | 0.8 | 0.8 | 0.8 | 0.8 |
| Carbonate Buffer | 1.3 | 2.0 | 2.0 | 1.8 |
| NHMI (1 mM) | 0.6 | 0.1 | 0.3 | 0.3 |

TABLE IV-continued

Bleaching on BC-1 by 4-Ethylbenzaldehyde with Various Initiators

|  | #1 | #2 | #3 | Average |
|---|---|---|---|---|
| 4-EBA (15 mM) | 1.0* | 0.5 | 1.1* | 0.9 |
| 4-EBA (15 mM) + NHMI (1 mM) | 1.4* | 0.3 | 1.2* | 1.0 |
| Carbonate Buffer | 1.5 | 2.1 | 1.8 | 1.8 |
| NHSI (1 mM) | 0.0 | 0.0 | 0.0 | 0.0 |
| 4-EBA (15 mM) | 1.0* | 1.2* | 1.0* | 1.1 |
| 4-EBA(15 mM) + NHSI (1 mM) | 1.2* | 1.3* | 1.4* | 1.3 |
| Carbonate Buffer | 2.3 | 1.9 | 2.2 | 2.1 |
| NHPI (1 mM) | −0.1 | 0.1 | −0.7 | −0.3 |
| 4-EBA (15 mM) | 1.8* | 1.8* | 1.9* | 1.8 |
| 4-EBA (15 mM) + NHPI (1 mM) | 10.5* | 10.6* | 10.5* | 10.5 |

Value for Carbonate Buffer = $\Delta R$
Value for Initiator = $\Delta(\Delta R)$
Value for 4-EBA = $\Delta(\Delta R)$
Value for 4-EBA + Initiator = $\Delta(\Delta R)$
* = Statistically significant bleaching over buffer alone ($\sigma_{ave} = 0.4$)

The structure of the various imide initiators is as follows:

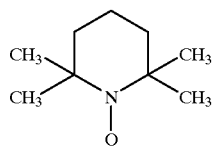

2,2,6,6-Tetramethyl-1-piperidinyloxy, Free radical (TEMPO)

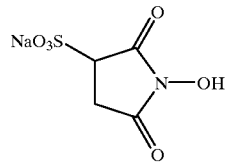

N-Hydroxysuccinimidesulfonic acid (NHSISA)

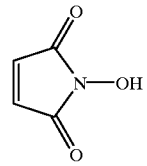

N-Hydroxymaleimide (NHMI)

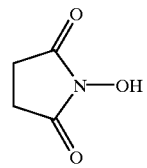

N-Hydroxysuccinimide (NHSI)

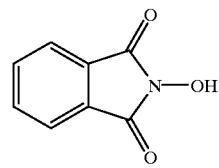

N-Hydroxyphthalimide (NHPI)

From Table IV it is seen that the cleaning of BC-1 tea stain by buffer alone is moderate ($\Delta\Delta R_{ave}$=1.8–2.1). Cleaning by various initiators alone was insignificant ($\Delta\Delta R_{ave}$=−0.3–0.3). Bleaching by 4-EBA alone was small and inconsistent ($\Delta\Delta R_{ave}$=0.5–1.8). However, bleaching by 4-EBA+ NHPI together was exceptionally high ($\Delta\Delta R_{ave}$=10.5). No bleaching was observed with 4-EBA+TEMPO. Slight bleaching was observed with 4-EBA+NHSISA, NHMI or NHSI. These results clearly demonstrate that initiator alone, and 4-EBA alone, do not effectively clean stubborn tea stains. By contrast, the addition of NHPI to 4-EBA in the presence of air, produces a system that bleaches BC-1 exceptionally well. The results suggest that bleaching was synergistic. For example, NHPI did not provide a cleaning benefit ($\Delta\Delta R_{ave}$=−0.2), and 4-EBA provided only a slight bleaching benefit ($\Delta\Delta R_{ave}$=1.8). The sum of these two benefits accounted for only 1.6 units. This was much less than the total bleaching ($\Delta\Delta R_{ave}$=10.5 units) provided by the aldehyde system (4-EBA+NHPI+Air). Also, it should be noted that the total cleaning was 12.6 (2.1+10.5), where 10.5 units were supplied by the aldehyde bleach system. This was an 83% cleaning improvement over carbonate buffer alone.

EXAMPLE 3

The following formulations are suitable for the cleaning of fabrics.

TABLE V

| | FORMULATION (% BY WEIGHT) | | | | |
|---|---|---|---|---|---|
| INGREDIENT | A | B | C | D | E |
| Capsuled 4-EBA | 40 | 32 | 15 | 25 | 10 |
| NHPI | 8 | 5 | 3 | 4 | 1 |
| Linear Alkylbenzene Sulphonate | 22 | 30 | 27.2 | 24.9 | 13.3 |
| Sodium Bicarbonate (pH 8) | 15 | 15 | 15 | 15 | 15 |
| Zeolite | — | — | 13.3 | 10 | 22 |
| Sodium Silicate | 1 | — | — | 3 | — |
| Water | 6.0 | 6.0 | 6.0 | 6.0 | 6.0 |
| Optical Brightener | 0.22 | 0.22 | 0.22 | 0.22 | 0.22 |
| Sodium Carboxymethylcellulose | 0.35 | 0.35 | 0.35 | 0.35 | 0.35 |
| Protease | 0.64 | 0.64 | 0.64 | 0.64 | 0.64 |
| Lipase | 0.14 | 0.14 | 0.14 | 0.14 | 0.14 |
| Sodium Sulphate | balance | balance | balance | balance | balance |

EXAMPLE 4

The following formulation illustrates a toilet bowl cleaning composition which may include the bleaching system of the present invention.

Toilet Bowl Cleaning Composition

| INGREDIENT | WEIGHT % |
|---|---|
| Sodium Acid Sulfate | 50–70 |
| Nonyl phenoxypolyethoxyethanol | 0–3 |
| Sodium Sulfate | 0–3 |
| 1,3-Dichloro-5,5-dimethylhydantoin | 0–10 |
| Sodium Chloride | 0–10 |
| Sodium Bicarbonate | 0–10 |
| Methyl Salicylate | 0–1 |
| Sodium alkyl benzene sulfonate | 0–2 |
| Sodium Xylene Sulfonate | 1–7 |
| Capsulated (4-ethylbenzaldehyde/2-ethylbenzaldehyde in 3:1 ratio) | 1–35 |
| NHPI | 0.1–8 |
| Water | Balance |

EXAMPLE 5

The following formulation illustrates a disinfectant cleaning composition which may include the bleaching system of the present invention.

Disinfectant Cleaning Composition

| INGREDIENT | WEIGHT % |
| --- | --- |
| Coconut Soap | 4–10 |
| O-Benzyl-p-chlorophenol | 1–5 |
| isopropanol | 0–10 |
| Pine Oil | 5–10 |
| Sodium Toluene Sulfonate | 4–15 |
| Methyl Salicylate | 0–3 |
| Capsulated (4-Methylbenzaldehyde/4-Ethylbenzaldehyde in 1:1 ratio) | 1–37 |
| NHPI | 0.1–8 |
| Water | Balance |

EXAMPLE 6

The following formulation illustrates a low alkalinity automatic dishwashing composition which may include the bleaching system of the present invention.

Low Alkalinity Automatic Dishwashing Composition

| INGREDIENT | WEIGHT % |
| --- | --- |
| Sodium Bicarbonate | to pH = 8 |
| Sodium Sulfate | 10–40 |
| Sodium Silicate | 0–30 |
| Nonionic Surfactant | 0–3 |
| Polyethylene Glycol | 0–5 |
| Sodium Benzene Sulfonate | 1–7 |
| Capsulated (4-Ethylbenzaldehyde) | 1–35 |
| NHPI | 0.1–6 |
| Water | Balance |

EXAMPLE 7

The following formulation illustrates an abrasive cleaning composition which may include the bleaching system of the present invention.

Abrasive Cleaning Composition

| INGREDIENT | WEIGHT % |
| --- | --- |
| Abrasive (Clay or Pumice) | 50–90 |
| Sodium Sulfate | 5–25 |
| Sodium Alkylbenzene Sulfonate | 0–4 |
| Sodium Bicarbonate | 1–25 or to pH = 8 |
| Sodium Stearate | 0–6 |
| Sodium Toluene Sulfonate | 1–10 |
| Capsulated (3-Methyl Benzaldehyde) | 5–30 |
| NHPI | 0.01–9 |
| Water | Balance |

EXAMPLE 8

The following formulation illustrates a hard-surface detergent cleaning composition which may include the bleaching system of the present invention.

Hard-Surface Detergent Cleaning Composition

| INGREDIENT | WEIGHT % |
| --- | --- |
| Potassium Sulfate | 1–20 |
| Potassium Toluene Sulfonate | 1–20 |
| Ammonia | To pH = 8 |
| Nonionic Surfactant | 0–5 |
| Naphtha | 1–30 |
| Pine Oil | 1–8 |
| Capsulated (2-Trifluoromethyl-benzaldehyde) | 1–30 |
| NHPI | 0.1–7 |
| Water | Balance |

EXAMPLE 9

The following formulation illustrates an oven cleaning composition which may include the bleaching system of the present invention.

Oven Cleaning Composition

| INGREDIENT | WEIGHT % |
| --- | --- |
| Sodium Orthosilicate | 0–11 |
| Chalk | 0–2 |
| Cellulose | 1–3 |
| N-Acetylethanolamine | 1–3 |
| Butylcellasolve | 1–3 |
| Sodium xylene sulfonate | 0.1–3 |
| Capsulated (2,4,6 Trimethyl/benzaldehyde) | 1–25 |
| NHPI | 0.1–8 |
| Water | Balance |

EXAMPLE 10

The following formulation illustrates a denture cleaning composition which may include the bleaching system of the present invention.

Denture Cleaning Composition

| INGREDIENT | WEIGHT % |
| --- | --- |
| Sodium Perborate | 0–33 |
| Sodium Chloride | 60–70 |
| Magnesium Sulfate | 2.5 |
| Calcium Chloride | 2.5 |
| Sodium Bicarbonate | to pH = 8 |
| Fragrance (Essential Oil) | 0.1–1 |
| Capsulated (3,4-Dimethylbenzaldehyde) | 0.1–15 |
| NHPI | 0.1–5 |
| Water | Balance |

EXAMPLE 11

The following formulation illustrates a hair lightening composition for dying hair blonde which may include the bleaching system of the present invention.

Hair Lightening Composition For Dying Hair Blonde

| INGREDIENT | WEIGHT % |
|---|---|
| Part 1 (Bottle 1) | |
| Capsulated (4-Ethylbenzaldehyde) | 43–57 |
| NHPI | 3–7 |
| Water | 40–50 |
| Part 2 (Bottle 2) | |
| Water | 50–70 |
| Propylene Glycol | 30–70 |
| Anionic Surfactant | 5–10 |
| Ammonia | 1–5 |
| p-Phenylenediamine | 0.3 |
| p-Methylaminophenol | 0.5 |
| p-Aminodiphenylamine | 0.15 |
| o-Aminophenol | 0.15 |
| Pyrocatechol | 0.25 |
| Resorcinol | 0.25 |
| Preservative | 0.1–1 |
| Dequest 2066 ® | 0.1–1 |
| Antioxidant | 0.1–1 |

The foregoing description and examples illustrate selected embodiments of the present invention. In light thereof variations and modifications will be suggested to one skilled in the art, all of which are within the spirit and purview of this invention.

What is claimed is:

1. A bleaching composition comprising:

(i) an effective amount for stain removal of a $C_7$–$C_{20}$ aromatic aldehyde;

(ii) air as a primary source of oxygen atoms to combine with the aldehyde; and (iii) an effective amount to activate the aldehyde of an imide having the formula:

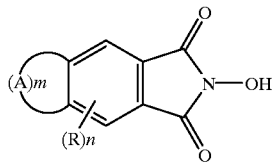

wherein

A is $CX_q$ and X is selected from the group consisting of hydrogen, $C_1$–$C_5$ alkyl, a heteroatom substituent and mixtures thereof, where q is independently 1 or 2;

R is a moiety selected from the group consisting of hydrogen, alkyl, cycloalkyl, aryl, alkoxy, hydroxy, acyloxy, halo, carboxy, amino, quaternary amino, sulpho, phospho, cyano radicals and mixtures thereof;

m and n independently range from 0 to 4.

2. The composition according to claim 1 wherein the imide is N-hydroxyphthalimide.

3. The composition according to claim 1 wherein the aromatic aldehyde is a liquid and contains from about 7 to 10 carbon atoms.

4. The composition according to claim 1 wherein the aromatic aldehyde is selected from the group consisting of 2-methylbenzaldehyde, 3-methylbenzaldehyde, 4-methylbenzaldehyde, 2-chlorobenzaldehyde, 3-trifluoromethylbenzaldehyde, 3,4-dimethylbenzaldehyde, 3,5-dimethylbenzaldehyde, 2,4-dimethylbenzaldehyde, 2,5-dimethylbenzaldehyde, 2-trifluoromethylbenzaldehyde, 2-ethylbenzaldehyde, 3-ethylbenzaldehyde, 4-ethylbenzaldehyde, 2,4,6-trimethylbenzaldehyde and mixtures thereof.

5. The composition according to claim 1 further comprising from about 1 to about 80% of a detergent builder.

6. The composition according to claim 1 further comprising from about 0.5 to about 50% of a surfactant.

7. The composition according to claim 1 further comprising an effective amount for cleaning of an enzyme selected from the group consisting of proteases, cellulases, lipases, amylases, peroxidases and mixtures thereof.

8. The composition according to claim 1 delivered in a form selected from the group consisting of a powder, sheet, pouch, tablet, aqueous liquid, nonaqueous liquid, aerosol, gel, cream and granules.

9. The composition according to claim 1 wherein the aromatic aldehyde is present in an amount from about 0.01 to about 80% and the imide is present in an amount from about 0.001 to about 65% by weight.

10. A method for bleaching a stained substrate, the method comprising contacting stained substrate in an aqueous medium in air with a $C_7$–$C_{20}$ aromatic aldehyde, a surfactant in an effective amount to clean the substrate and with an imide whose structure is:

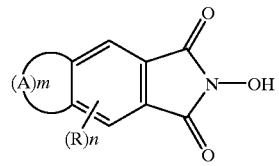

wherein

A is $CX_q$ and X is selected from the group consisting of hydrogen, $C_1$–$C_5$ alkyl, a heteroatom substituent and mixtures thereof, where q is independently 1 or 2;

R is a moiety selected from the group consisting of hydrogen, alkyl, cycloalkyl, aryl, alkoxy, hydroxy, acyloxy, halo, carboxy, amino, quaternary amino, sulpho, phospho, cyano radicals and mixtures thereof;

m and n independently range from 0 to 4.

11. The method according to claim 10 wherein the aromatic aldehyde and imide are present in a weight ratio of about 1000:1 to about 10:1.

12. The method according to claim 10 wherein the substrate is selected from the group consisting of fabrics, household fixtures and kitchenware.

13. The method according to claim 10 wherein the substrate is a denture.

14. A method for bleaching a stained substrate, the method comprising contacting the stained substrate in air in an aqueous medium with a $C_7$–$C_{20}$ aromatic aldehyde and an imide having the structure:

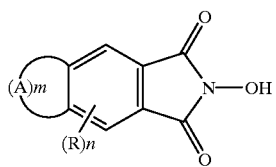

wherein
A is $CX_q$ and X is selected from the group consisting of hydrogen, $C_1$–$C_5$ alkyl, a heteroatom substituent and mixtures thereof, where q is independently 1 or 2;
R is a moiety selected from the group consisting of hydrogen, alkyl, cycloalkyl, aryl, alkoxy, hydroxy, acyloxy, halo, carboxy, amino, quaternary amino, sulpho, phospho, cyano radicals and mixtures thereof;
m and n independently range from 0 to 4.

* * * * *